United States Patent [19]

Williams et al.

[11] Patent Number: 5,016,645
[45] Date of Patent: May 21, 1991

[54] MEDICAL ELECTRODE LEAD

[76] Inventors: Terrell Williams, 1444 - 97th Ave. NW., Coon Rapids, Minn. 55433; John G. Keimel, 1888 9th St. NW., New Brighton, Minn. 55112; Roger Rugland, 1935 134th La. NE., Anoka, Minn. 55303; Richard Sandstrom, 12959 Mayberry Trail N., Scandia, Minn. 55073; Timothy Holleman, 13600 Yancy St., Ham Lake, Minn. 55303

[21] Appl. No.: 264,916

[22] Filed: Oct. 31, 1988

Related U.S. Application Data

[63] Continuation-in-part of Ser. No. 63,371, Jun. 18, 1987, Pat. No. 4,817,634.

[51] Int. Cl.$^5$ ............................................. A61N 1/05
[52] U.S. Cl. ................................. 128/784; 128/785; 128/798; 128/799
[58] Field of Search .......................... 128/785–786, 128/798, 799, 419 D, 804, 784

[56] References Cited

U.S. PATENT DOCUMENTS

| | | | |
|---|---|---|---|
| 724,913 | 4/1903 | Montgomery | 604/278 |
| 3,942,536 | 3/1976 | Mirowski et al. | 128/419 D |
| 4,030,509 | 6/1977 | Heilman et al. | 128/419 D |
| 4,161,952 | 7/1979 | Kinney et al. | 128/786 |
| 4,291,707 | 9/1981 | Heilman et al. | 128/784 |
| 4,641,656 | 2/1987 | Smits | 128/419 D |
| 4,817,634 | 4/1989 | Holleman et al. | 128/785 X |
| 4,827,932 | 5/1989 | Ideker et al. | 128/785 |

FOREIGN PATENT DOCUMENTS

| | | |
|---|---|---|
| 0211166 | 5/1986 | European Pat. Off. . |
| 2182566 | 5/1987 | United Kingdom . |

OTHER PUBLICATIONS

Brochure entitled "Medtronic Myocardial Pacing Lead Model 5815A", MC 760589b, Apr. 1979, by Medtronic, Inc.
Article entitled "Post-Operative Variations in the Electrophysiology of the Epicardial Onlay Pacemaker Lead", by Nicholas P. D. Smyth, M.D., *Medical Annals of the District of Columbia*, vol. 40, No. 1, Jan. 1971, pp. 12–15.

*Primary Examiner*—Ruth S. Smith

[57] ABSTRACT

A medical electrode lead employing one or more elongated electrode coils embedded in the surface of a flexible base pad. The electrode coils take the form of space wound coils following tortuous paths over the surface of the base pad to provide a large surface area electrode. The electrode coils include a plurality of spaced, generally parallel electrode coil segments. Located intermediate adjacent the parallel electrode coil segments are grooves or pleats, molded into the base pad. These grooves or pleats provide increased elasticity of the electrode and increased ability to conform to the contours of the heart. Insulative cores taking the form of plastic tubes are located within the electrode coils to prevent tissue ingrowth between the individual electrode coils, without induly reducing flexibility of the electrode.

9 Claims, 4 Drawing Sheets

MEDICAL ELECTRODE LEAD

CROSS REFERENCE TO COMMONLY OWNED CO-PENDING APPLICATION

This application is a continuation-in-part of U.S. Pat. No. 4,817,634 for an "EPICARDIAL PATCH ELECTRODE", issued Apr. 4, 1989 to Holleman, Sandstrom, Rugland and Williams. This prior application is also incorporated by reference herein in its entirety.

BACKGROUND OF THE INVENTION

This invention relates to medical electrical stimulation electrode leads in general and to epicardial defibrillation electrode leads in particular.

In the past years, there has been substantial activity directed toward development of a practical, implantable defibrillator. Some approaches, such as disclosed in U.S. Pat. No. 3,942,536, issued to Mirowski et al, and U.S. Pat. No. 4,161,952, issued to Kinney et al have employed only endocardial electrodes. However, more recent approaches to this problem have focused on systems employing one or more epicardial electrode leads as alternatives to or in addition to endocardial electrodes. Some such systems are disclosed in U.S. Pat. No. 4,030,509, issued to Heilman et al, and U.S. Pat. No. 4,291,707, issued to Heilman et al.

Generally, an epicardial defibrillation electrode must accomplish two important functions. First, it must deliver a relatively large amount of electrical energy to the heart with a minimal amount of tissue damage. For this reason, it is generally believed that epicardial defibrillation electrodes should have a large electrode surface area in order to distribute the energy over a wide area of the heart. The use of large surface electrodes reduces the density of the current applied to the heart, reducing the potential for damage to heart tissue. In addition, use of electrodes extending over a large area of the heart is believed to assist in improving current distribution through the heart tissue, reducing resistance and reducing the amount of energy which must be applied to the heart. For this reason, many prior art leads have employed electrodes having large surface areas and having individual, dispersed conductive areas.

The large size of epicardial defibrillation electrodes itself creates a problem. Motion of the heart during contraction is complex, and has been likened to a "wringing" action. A large surface area electrode must be capable of conforming to the contours of the heart and to changes in contours of the heart in order to continue to function properly. Typical prior art epicardial defibrillation leads, as disclosed in U.S. Pat. No. 4,030,509, issued to Heilman et al, however, employ large surface electrodes in the form of screens or plates which limit the flexibility of the electrode pad. One alternative to the use of screens and plates is disclosed in U.S. Pat. No. 4,641,656 issued to Smits et al which discloses electrode pads having spaced contact areas separated by perforations or indentations which allow the individual conductive areas to move with respect to one another.

In the above cited parent application to the present case, an epicardial defibrillation lead is disclosed employing a plurality of electrode coils mounted within grooves molded into a flexible, insulative base pad. In some embodiments, the electrode coils are simply glued into the grooves. In other embodiments, a solid, insulative core is provided and the insulative core is bonded to the electrode pad, holding the electrode coils in place.

SUMMARY OF THE INVENTION

The present invention addresses the problems of even current distribution, electrode flexibility and electrode flex life by use of one or more space wound electrode coils, mounted in grooves molded into a thin, flexible base pad. The periphery of the pad takes the general form of a closed, convex curve. Rather than being provided with perforations or indentations as in Smits et al, the base pad is provided with grooves or pleats intermediate the grooves in which the electrode coils are mounted. This provides additional elasticity to the base pad and allows the pad to more readily be shaped to conform to three dimensional configurations, such as the surface of the heart.

In addition, current distribution in the present lead is improved over the lead disclosed in the above cited parent application. The inventors have determined that in use, current delivery tends to be concentrated around the edge of a base pad, leading to higher current densities at each of the individual coils of the outermost electrode coils. For this reason, in the present lead, the electrode coils adjacent the exterior periphery of the electrode pad are provided with an increased number of individual coils per unit of lineal measure, to provide a larger electrode surface area and to reduce the possibility of burns or tissue damage associated with high current densities.

Finally, the electrode coils of the present lead are provided with insulative cores, which extend through the lumens of the electrode coils, preventing tissue ingrowth between individual coils. Unlike the cores employed in the above-cited parent application, the cores take the form of tubes of silicone rubber, which are believed to restrict the flexibility of the electrode less than solid cores.

Although the electrode lead is disclosed in an embodiment particularly adapted for use as an epicardial defibrillation electrode, the invention is also believed useful in other contexts, and in particular is believed useful as a subcutaneous defibrillation electrode lead. In this application, flexibility of the electrode and the ability to conform the changing shapes of the tissue surrounding the electrode is also believed desirable. Similarly, electrode leads according to the present invention may be useful in the context of muscle or nerve stimulation in applications in which electrode flexibility is particularly desirable.

DETAILED DESCRIPTION OF THE DRAWINGS

Figure 1:
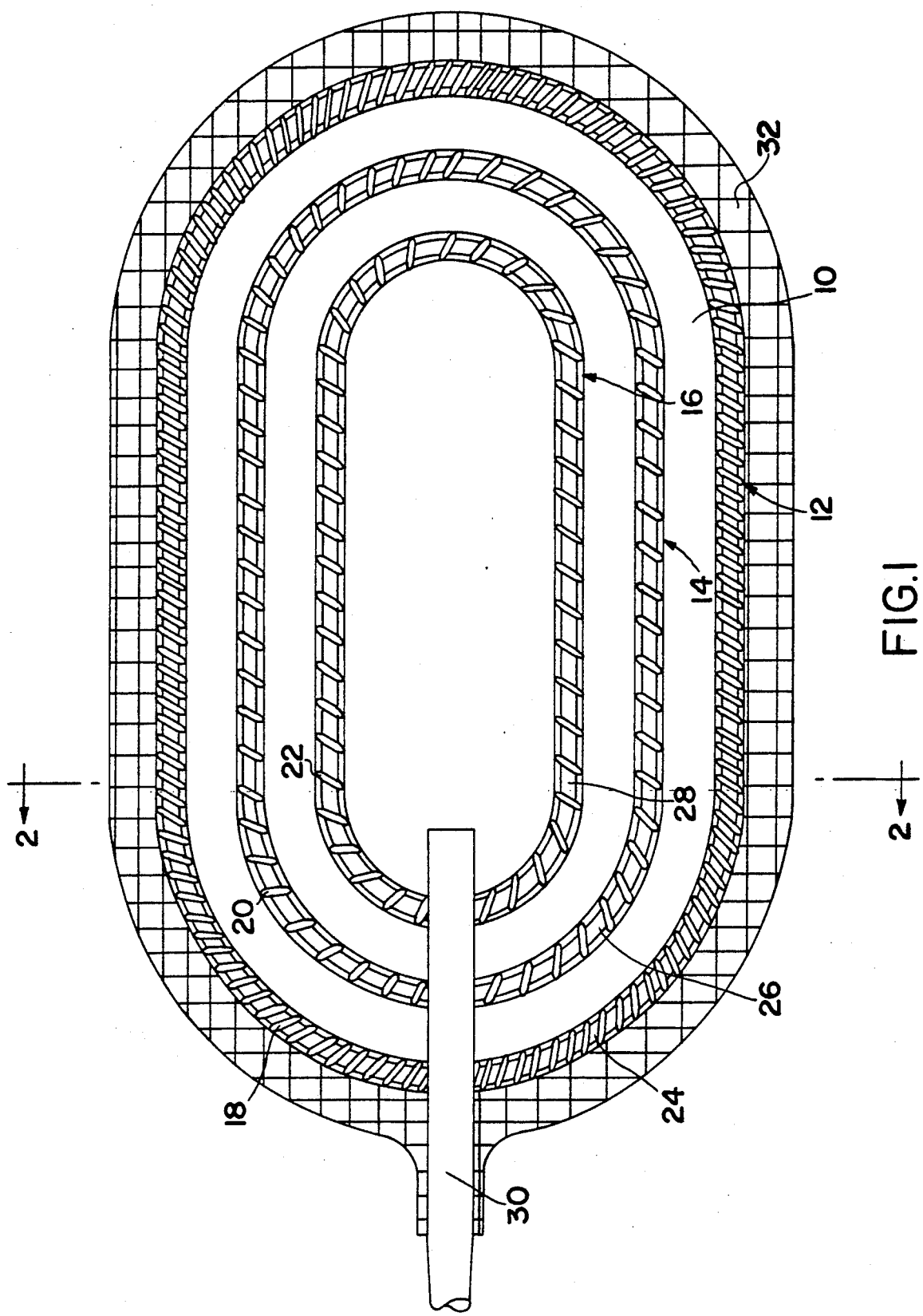
FIG. 1 shows a plan view of the lower surface of an electrode lead according to the present invention.

FIG. 1 shows a plan view of a first embodiment of a defibrillation electrode lead according to the present invention. The lower surface of the distal end of the lead is illustrated.

The lead is provided with a flexible base pad 10 having a generally oval configuration. Base pad 10 has molded therein three concentric, generally oval grooves 12, 14 and 16. The thickness of base pad 10 is preferably less than the depth of grooves 12, 14 and 16. Base pad 10 is preferably molded of a flexible, elastic, insulative material such as silicone rubber. Located within grooves 12, 14 and 16, respectively, are electrode coils 18, 20 and 22. Electrode coils 18, 20 and 22 take the form of space wound single or multifilar coils of a biocompatible, highly conductive metal such as platinum. In defibrillation electrodes, or other electrodes for delivery of high current levels, it is desirable to avoid "hot spots" or areas of high current density which may cause burning. Testing has indicated that in use, the highest concentration of current density will occur around the periphery of base pad 10. Therefore, in order to reduce the current density associated with the individual turns of electrode coil 18, it is provided with approximately twice the number of individual turns per unit of lineal measure as compared to electrode coils 20 and 22. This can be accomplished either by doubling the number of filars in electrode coil 18 or by decreasing the pitch of electrode coil 18. If the pitch is decreased, the cross section of the wire used to fabricate electrode coil 18 should be doubled to avoid an increase in electrode impedance.

Located within the lumens of coils 18, 20 and 22 are silicone rubber tubes 24, 26 and 28. The outer diameter of tubes 24, 26 and 28 closely corresponds to the diameter of the lumen through coils 18, 20 and 22. Tubes 24, 26 and 28 prevent tissue ingrowth between the individual turns of coils 18, 20 and 22. This feature allows for the electrode to be removed even after extended periods of implant.

Coils 18, 20 and 22 are retained within base pad 10 by means of medical adhesive which bonds tubes 24, 26 and 28 to base pad 10. The medical adhesive also prevents tissue from growing around tubes 24, 26 and 28.

Electrode coils 18, 20 and 22 are coupled to an elongated insulated conductor 30, which terminates at its proximal end in a connector pin of the type typically used to connect electrical leads to implantable pulse generators. Any appropriate method of connection such as welding, crimping or swaging may be used to interconnect conductor 30 with electrode coils 18, 20 and 22. One particular method is set forth in the parent application to the present case, which has been incorporated by reference.

A Dacron reinforcing mesh 32 has been molded into base pad 10, around the periphery of the pad, exterior to the outer most electrode coil 18. This reinforcing mesh allows for the edge of base pad 10 to be sutured to the heart, while reducing the chances of tearing or fraying base pad 10. Mesh 32 is limited to the periphery of the electrode to allow for flexibility of the electrode in the vicinity of base pad 10. Because the heart is a three dimensional surface, it is desirable to allow the electrode to assume a three dimensional configuration. While mesh 32 essentially fixes the outer diameter of base pad 10, the inherent elasticity and flexibility of the silicone rubber of which base pad 10 is molded allows for some stretching intermediate the electrode coils 18, 20 and 22. This allows the electrode to conform to some degree to the three dimensional configuration of the heart. Limiting mesh 32 to the periphery of the electrode also allows for some stretching of the base pad along both the short and long axes of base pad 10. In conjunction with the desire for flexibility, the use of silicone rubber tubes 24, 26 and 28 in preference to solid cores or cores of inelastic, insulative material is also preferred.

Figure 2:
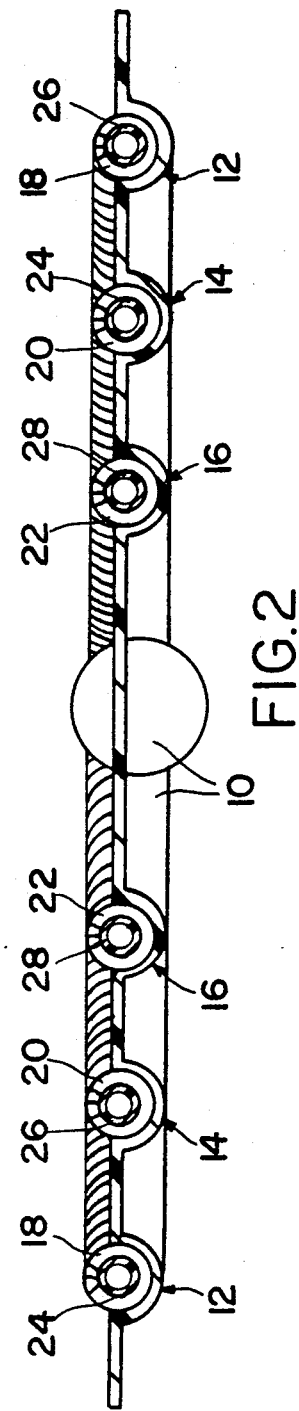
FIG. 2 shows a cross-section of the lead of FIG. 1.

FIG. 2 shows a cross sectional view of the electrode lead of FIG. 1. In this view, it can clearly be seen that grooves 12, 14 and 16 are substantially deeper than the thickness of base pad 10. The relationship of electrode coils 18, 20 and 22 to tubes 24, 26 and 28 and to electrode pad 10 is also visible. Preferably, grooves 12, 14 and 16 are generally semicircular, and have approximately the same radius as coils 18, 20 and 22. The individual turns of coils 18, 20 and 22 extend approximately ⅛ to ⅓ their diameter from the lower surface of electrode pad 10. The adhesive which couples tubes 24, 26 and 28 to base pad 10 is not illustrated in this figure, for the sake of clarity. However, it preferably fills the gaps between base pad 10 and the tubes 24, 26 and 28.

Figure 3:
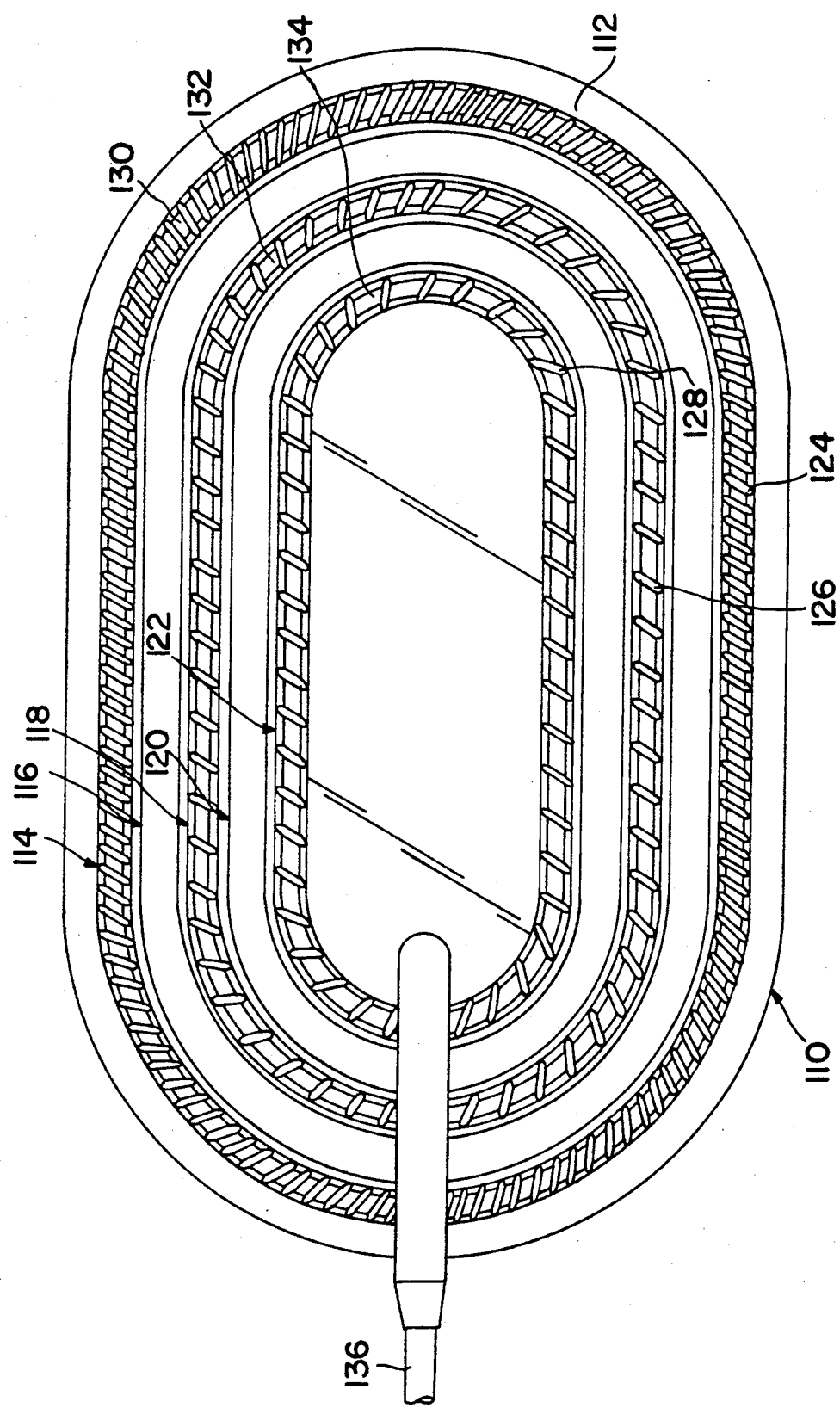
FIG. 3 shows a plan view of the lower surface of an alternate embodiment of an electrode lead according to the present invention.

FIG. 3 shows a plan view of a second embodiment of a defibrillation electrode lead according to the present invention. The base pad 110 is molded of silicone rubber and displays a generally oval configuration. Around its outer periphery, pad 110 may include a woven dacron or other fabric mesh 112. Preferably, mesh 112 is limited to the outer periphery of the base pad 110, to allow the interior of the pad 110 to more readily stretch across its width and to more readily conform to the three dimensional surface of the heart. Molded into the pad 110 are a plurality of semicircular grooves 114, 116, 118, 120 and 122. Located within grooves 114, 118 and 122 are electrode coils 124, 126 and 128. In this view, it can be seen that electrode coils 124, 126 and 128 define a plurality of generally parallel coil segments. Electrode coils 124, 126 and 128 take the form of single or multifilar space wound coils of biocompatible, inert conductive metal. Platinum or other biocompatible metals having low electrical resistance are preferred. The outermost electrode coil (in this case 124) has a greater number of turns per unit of lineal measure to decrease current density at individual points of contact with the heart. In some cases, for example, in electrode pads carrying four or more concentric electrode coils, it may be desirable to have the number of turns per unit of lineal measure increased with regard to the outer two electrode coils.

Mounted within the electrode coils are insulative tubular cores 130, 132 and 134, which correspond to tubes 24, 26 and 28 (FIG. 1). The provision of insulative cores 130, 132 and 134 has the disadvantage that it reduces the ability of the base pad 110 to be elongated in the vicinity of the electrode coils. As such, in some cases, it may be desirable to provide an alternative method of imparting elasticity and conformability to pad 110. In the present invention, grooves 116 and 120 provide this additional elasticity.

Grooves 116 and 120, as illustrated, are semicircular grooves, identical in cross section to grooves 114, 118 and 122. This allows for extraordinary flexibility in the construction of the electrode, as it allows for a single molded base pad to accommodate a variety of number of electrode coils, and allows each groove to be used to mount an electrode coil, if so desired. However, while this is particularly beneficial from a manufacturing viewpoint, it is not necessary for the function of the electrodes. Grooves 116 and 120 may display a variety of cross sectional configurations, including triangular, square, or pleated. In order for the invention to function, it is only necessary that the depths of the indentations of grooves 116 and 120 must exceed the thickness of base pad 110. This will allow pad 110 to stretch, as grooves 116 and 120 assume a more planar configuration. The ability of pad 110 to stretch in the areas of grooves 116 and 120 allows the pad 110 to assume a humped or rounded non-planar configuration.

Grooves 116 and 120, located between generally parallel segments of electrode coils 124, 126 and 128 allow for increased elasticity perpendicular to the electrode coils. For example, in the configuration illustrated in FIG. 3, the grooves allow for substantial lateral expansion of the electrode pad 110, in a direction perpendicular to the axis of conductor 136. If it is desired that the ability to stretch pad 110 along the axis of conductor 136 be roughly equal to the ability to stretch perpendicular to that axis, pad 110 and its grooves should be molded to display a more square or circular configuration.

Grooves 116 and 120 also allow for movement of the coil wires 130, 132 and 134 within the surface generally defined by electrode pad 110. This allows base pad 110 to more easily assume a three dimensional configuration. For example, electrode coil 134 could be displaced from electrode coil 132 and electrode coil 132 displaced from electrode coil 130 along an axis perpendicular to the general plane of pad 110. This allows the pad to assume a humped, three dimensional configuration, rather than a generally planar configuration. Because the heart displays a generally three dimensional configuration which changes during heartbeats, this flexibility is believed especially desirable. The reinforcing mesh 112, of course, limits the extensibility of the outer circumference of pad 110.

Figure 4:
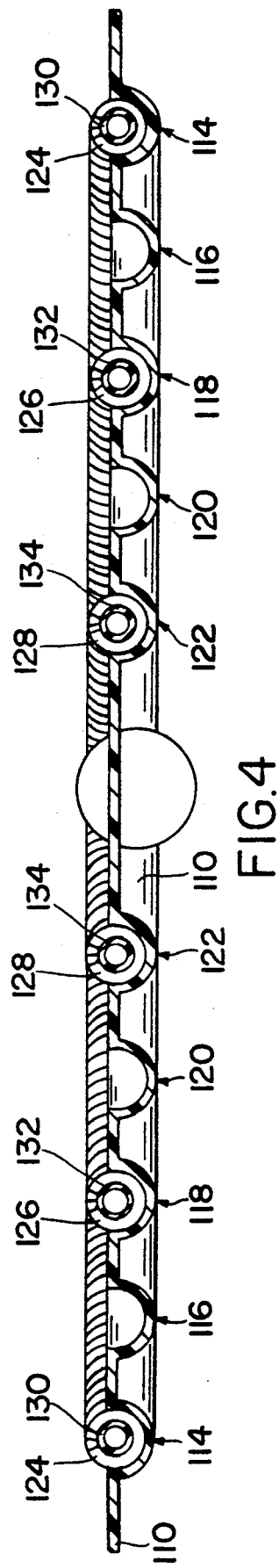
FIG. 4 shows a cross-section of the lead of FIG. 3.

FIG. 4 shows a cross section of the lead of FIG. 3. All of the components illustrated in FIG. 4 are numbered according to the identical component illustrated in FIG. 3.

In this view, it can be seen that the thickness of the pad 110 is substantially less than the diameter of the electrode coils 124, 126 and 128. Moreover, the thickness of pad 110 is less than the depths of grooves 114, 116, 118, 120 and 122. This is particularly important in conjunction with grooves 116 and 120, in that it allows for the electrode coils mounted within grooves 114, 118 and 122 to be displaced from one another as grooves 116 and 120 are stretched.

In this view, it can also be seen that insulative cores 130, 132 and 134 take the form of hollow tubes of plastic. Preferably, silicone rubber or other elastoplastic is used to fabricate tubes 130, 132 and 134. Intermediate the individual turns of electrode coils 124, 126 and 128, medical adhesive is used to bond cores 130, 132 and 134 to electrode pad 110.

Figure 5:
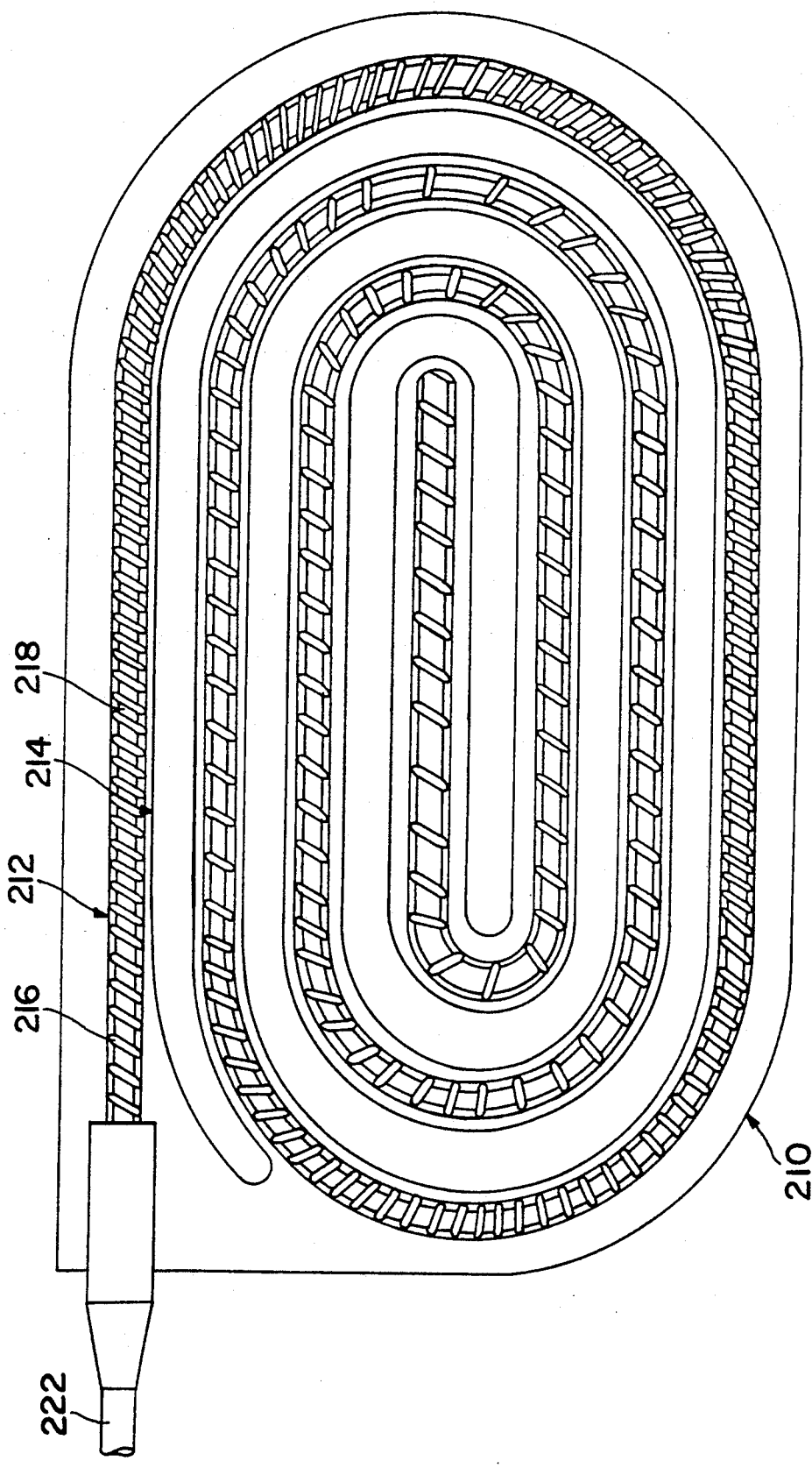
FIG. 5 shows a plan view of a third embodiment of an electrode lead according to the present invention.

FIG. 5 shows a third embodiment of an electrode lead according to the present invention. In FIG. 5, the base pad 210 is provided with two generally parallel elongated grooves 212 and 214 which spiral in toward the center of pad 210. An electrode coil 16 is located in one of the grooves 212. A tubular insulative core 18 is located within coil 216, and is held in place within pad 210 by medical adhesive, as discussed in conjunction with FIGS. 1–4 above.

The configuration of the electrode lead illustrated in FIG. 5 is also believed beneficial in providing a highly flexible electrode capable of assuming three dimensional configurations. Like the electrode pad of FIGS. 3 and 4, it provides an alteration of relatively less elastic areas in the immediate vicinity of the electrode coil 216 with more elastic areas, comprising groove 214. This electrode, like the electrode of FIG. 3, is capable of assuming humped, three dimensional configurations, and should in fact somewhat more readily assume three dimensional configurations than the electrode of FIG. 3.

The periphery of base pad 210 may be provided with a reinforcing Dacron mesh 220, corresponding to the Dacron mesh discussed in conjunction with FIG. 1, above. Again, the mesh 220 should be limited to the periphery of pad 210. Electrode coil 216 is coupled to an elongated insulative conductor 222, which extends to an electrical connector assembly (not illustrated) of the type typically used to couple an implantable electrical lead to a pulse generator. Similarly, the problem of increased current density at the periphery of base pad 210 can be addressed by either increasing the pitch of electrode coil 216 for a limited portion of its length, where it is adjacent the periphery of base pad 210 or by increasing the number of filars of electrode coil 216 along that portion of its length which is adjacent the exterior periphery of base pad 210.

The embodiments shown above are intended to be illustrative of the invention, and not to restrict the scope of the claims. Other appropriate physical configurations, including other electrode pad shapes, different numbers of electrode coils, and other configurations for the grooves intermediate the electrode coils are also believed to be within the scope of the present invention.

The advantages of the electrodes of FIGS. 3, 4 and 5 in particular may be achieved using a variety of configurations. For example, a plurality of individual electrode coils which do not form closed loops be substituted for a plurality of electrode coils which form closed loops as in FIG. 3, or for the single spiraled electrode coil of FIG. 5. Similarly, it is not necessary that the grooves intermediate the electrode coils be continuous over the surface of the base pad. A plurality of discrete molded grooves can provide a similar benefit.

Although all of the embodiments illustrated employ grooves molded into the base pad which have the same orientation as the grooves which retain the electrode coils, it is also possible to additionally or alternatively employ grooves molded in the upper surface of the base pad, as long as they provide similar areas of increased flexibility and extensibility intermediate the electrode coils.

Although all of the embodiments illustrated employ base pads fabricated of insulative material and employ electrodes taking the form of coils, the invention may also be useful in conjunction with electrodes taking different forms. For example, in some applications, it may be desirable that the base pad itself is conductive, or at least semiconductive. Although in the context of a defibrillation electrode, it is believed that the electrode coils illustrated provide an appropriate electrode surface, in other applications, other conductive metallic or nonmetallic materials may be used to provide corresponding electrode surfaces. For example, conductive polymers, metallization layers, braided or tinsel wires, wire mesh or carbon fibers may be appropriate, provided that the electrode surfaces define a plurality of parallel electrode paths, and that means for increasing the flexibility of the electrode, such as grooves, are located between the electrode paths.

In conjunction with the above description, we claim:

1. A medical electrical lead comprising:
an elastic base pad having an outer periphery;
means for reinforcement mounted to said base pad and limited to the periphery of said base pad, said reinforcement means comprising a fabric mesh;
a plurality of spaced electrodes which take the form of segments of one or more elongated electrode coils arrayed on said base pad interior to said reinforcement means, said base pad free of said reinforcement means in the spaces intermediate said electrodes.

2. An improved medical electrical lead comprising a flexible base pad carrying one or more elongated electrode coils defining one or more elongated paths along said flexible base pad, said one or more electrode coils including outer coil segments adjacent the periphery of said electrode base pad and inner coil segments, located interior to said outer coil segments, wherein:
said outer coil segments have an increased number of individual turns per unit of lineal measure as compared to said inner coil segments.

3. An improved medical electrode lead comprising a flexible base pad and one or more elongated electrode coils mounted to said flexible base pad, each of said electrode coils being a space wound coil having a central lumen, said lead further comprising elongated flexible cores located within the lumens of said one or more electrode coils, wherein:
said flexible cores are elastic plastic tubes.

4. A medical electrical lead comprising a flexible base pad and one or more electrode coils mounted to said base pad, said one or more electrode coils defining a plurality of generally parallel electrode coil segments, spaced from one another, wherein:
said base pad is provided with means for facilitating expansion of said base pad, in the areas of said base pad intermediate said parallel electrode coil segments.

5. A lead according to claim 4 wherein said means for facilitating expansion of said base pad comprises one or more elongated grooves, formed in said base pad, intermediate said generally parallel segments of said one or more electrode coils, said grooves having a depth greater than the thickness of said base pad.

6. A lead according to claim 5 wherein said one or more electrode coils comprises a plurality of electrode coils taking the form of closed curves, mounted concentrically within one another, on said base pad.

7. An electrode according to claim 5 wherein said one or more electrode coils comprise an elongated electrode coil generally taking the form of a spiral.

8. A medical electrical lead comprising a flexible base pad including electrode means for delivery of electrical current, said electrode means defining a plurality of generally parallel elongated electrode segments, said base pad further provided with means for facilitating the expansion of said base pad in the areas of said base pad intermediate said parallel elongated electrode segments, said means for facilitating expansion comprising one or more elongated grooves formed in said base pad, intermediate said generally parallel elongated electrode segments, said grooves having a depth greater than the thickness of said base pad; and
an elongated electrical conductor electrically coupled to said electrode segments on said base pad.

9. An electrode according to claim 8 wherein said base pad is insulative and wherein said electrode segments are formed of a conductive material differing from the material of said base pad.

* * * * *